United States Patent [19]

Horiuchi et al.

[11] Patent Number: 5,068,190

[45] Date of Patent: Nov. 26, 1991

[54] N-ACETYLHEXOSAMINE-DEHYDROGENASE, PROCESS FOR PRODUCING SAME, METHOD FOR THE QUANTITATIVE ANALYSIS OF N-ACETYLGLUCOSAMINE OR N-ACETYLGALACTOSAMINE USING SAME AND KIT FOR USE IN THE QUANTITATIVE ANALYSIS

[75] Inventors: Tatsuo Horiuchi, Nagareyama; Toshiko Kurokawa, Noda, all of Japan

[73] Assignee: Noda Institute for Scientific Research, Noda, Japan

[21] Appl. No.: 407,150

[22] Filed: Sep. 14, 1989

[30] Foreign Application Priority Data

Sep. 21, 1988 [JP] Japan .................. 63-234746

[51] Int. Cl.$^5$ ............... C12N 9/04; C12Q 1/32
[52] U.S. Cl. ..................... 435/190; 435/183; 435/26; 435/810; 435/262; 435/875; 435/7.9; 435/7.91; 435/7.95
[58] Field of Search ............ 435/26, 190, 183

[56] References Cited

U.S. PATENT DOCUMENTS 4,634,663  1/1987  Horiuchi ................... 435/25
4,960,701  10/1990  Horiuchi et al. .......... 435/190

FOREIGN PATENT DOCUMENTS 59-156299  4/1984  Japan .

OTHER PUBLICATIONS

Chemical Abstracts, 101:22633g, 405 (1984).
Chemical Abstracts, 102:60787W, 481 (1985).
Horiuchi et al., "Purification and Characterization of N-Acetyl-D-Hexosamine Dehydrogenase from Pseudomonas sp. No. 53", Agric. Biol. Chem. 53, 1919-25 (1989).

*Primary Examiner*—Robert A. Wax
*Assistant Examiner*—M. P. Woodward
*Attorney, Agent, or Firm*—Banner, Birch, McKie & Beckett

[57] ABSTRACT

N-Acetylhexosamine-dehydrogenase which takes off hydrogen from N-acetylglucosamine or N-acetylgalactosamine to convert them to N-acetylglucosaminolactone or N-acetylgalactosaminolactone, respectively, and, at the same time, reduces co-enzymes NAD$^+$ to NADH is provided herein.

The enzyme of this invention can be obtained by culturing, in a medium, a strain belonging to Genus Pseudomonas and having an ability to produce N-acetylhexosamine-dehydrogenase, followed by collecting the enzyme from the cultured product.

Herein is also provided a method for quantitatively analyzing N-acetylglucosamine or N-acetylgalactosamine which comprises reacting N-acetylglucosamine-dehydrogenase upon a sample containing N-acetylglucosamine or N-acetylgalactosamine and measuring the quantity of the resulting NADH.

5 Claims, 3 Drawing Sheets

N-ACETYLHEXOSAMINE-DEHYDROGENASE, PROCESS FOR PRODUCING SAME, METHOD FOR THE QUANTITATIVE ANALYSIS OF N-ACETYLGLUCOSAMINE OR N-ACETYLGALACTOSAMINE USING SAME AND KIT FOR USE IN THE QUANTITATIVE ANALYSIS

BACKGROUND OF THE INVENTION

1. Field of the Invention

This invention relates to a novel N-acetyl hexosamine-dehydrogenase (hereinafter referred to as N-AHDH) which acts upon N-acetylglucosamine or N-acetyl galactosamine to convert them to N-acetylglucosamino lactone or N-acetylgalactosaminolactone and, at the same time, reduces the oxidized form of nicotinamide adenine dinucleotide (NAD+), to the reduced form of nicotinamide adenine dinucleotide (NADH). This invention relates also to a process for producing said N-AHDH, an enzymatic method for quantitatively analyzing N-acetylglucosamine or N-acetylgalactosamine by the use of N-AHDH, and a kit for use in the quantiative analysis.

2. Description of the Prior Art

Since the discovery of the fact that complex sugars or glycoconjugates present in the surface layer of cells and body fluids in combination to protein or the like carries the informations for controlling living body, the studies of complex sugars or glycoconjugates has made a rapid progress. As the result, the relation between abnormal control of living body and structural abnormality of complex sugars or glycoconjugates has gradually been elucidated.

On the other hand, mucopolysaccharides are sometimes excreted into urine largely or accumulated in tissues due to the metalbolic abnormality of mucopolysaccharides of complex sugars, so that it is important to study the structure of these sugars in order to specify its cause.

In clinical tests, enzymatic activity of N-acetylglucosamine metabolic system, i.e. the activities of $\beta$-N-acetylglucosaminidase and lysozyme, are actively measured in order to specify the extent and location of disorder in kidney.

In these studies and measurements of enzyme activity, quantitative analysis of N-acetylglucosamine plays an important role. Thus, an excellent method for its measurement has been desired among specialists in the art.

Generally, quantitative analysis of N-acetylglucosamine is carried out by chemical methods such as Morgan-Elson method, etc. However, methods using an enzyme are superior in accuracy and simplicity. As one example, the method of Japanese Patent Application Kokai No. 59-156299 using N-acetylhexosamine-oxidase can be referred to. According to this method, N-acetylhexosamine is quantitatively analyzed by reacting N-acetylhexosamine with N-acetylhexosamine-oxidase and determining the resulting product such as hydrogen peroxide and the like or by determining the quantity of oxygen absorbed with progress of the reaction.

However, since N-acetylhexosamine-oxidase has a relatively broad substrate specificity, it exercises an action upon N,N'-diacetylchitobiose and the like, too. Since this sugar forms two molecules of N-acetylglucosamine upon one reaction with $\beta$-N-acetylglucosaminidase, it is usable as an excellent substrate for use in high sensitivity measurement of enzyme activity. However, it has been unusable as a substrate for measurement of $\beta$-N-acetylglucosaminidase in urine for the above-mentioned reason.

It is also known that the reductive substances present in urine exercise an influence on the quantitative analysis system of hydrogen peroxide, and accuracy of measurement is somewhat deteriorated by it. However, it is known that, in case of quantitative analysis system of NADH, these substances hardly exercise such an influence. Accordingly, the pre-treatment of sample and devices exerted on measuring system can be minimized and a measurement of higher accuracy can be practised.

SUMMARY OF THE INVENTION

Taking notice of this point, the present inventors have searched an enzyme usable in the quantitative analysis of N-acetylglucosamine, with the aim of developing an improved enzymatic measurement of N-acetylhexosamine. As the result, it has been found that a bacterium belonging to Genus Pseudomonas isolated from soil contains a novel enzyme N-AHDH which acts upon N-acetylglucosamine or N-acetylgalactosamine to convert them to N-acetylglucosaminolactone or N-acetylgalactosaminolactone, respectively, and, at the same time, reduces the NAD+ existing in the system to NADH. It was confirmed that this enzyme does not act upon acetylchitobiose and it is usable in a novel method for enzymatic quantitative analysis of N-acetylglucosamine and N-acetylgalactosamine. Based on these findings, this invention has been accomplished.

Thus, this invention relates to a novel enzyme N-AHDH which acts upon N-acetylglucosamine and N-acetylgalactosamine to convert them to N-acetylglucosaminolactone and N-acetylgalactosaminolactone, respectively, and, at the same time, reduces NAD+ to NADH, as well as to a process for producing N-AHDH which comprises culturing, in a medium, a strain belonging to Genus Pseudomonas and having an ability to produce N-AHDH and collecting N-AHDH from the cultured product.

Further, this invention relates also to a method for the quantitative analysis of N-acetylglucosamine or N-acetylgalactosamine which comprises reacting N-AHDH upon a sample containing N-acetylglucosamine or N-acetylgalactosamine and measuring the resulting NADH, as well as to a quantitative analysis kit comprising at least N-AHDH, NAD+ and buffer solution.

DESCRIPTION OF THE PREFERRED EMBODIMENTS

Next, this invention will be explained more concretely.

Physico-chemical properties of the novel enzyme N-AHDH of this invention are as mentioned below.

(1) Action and Substrate Specificity

As shown in the following reaction scheme, this enzyme oxidizes N-acetylglucosamine or N-acetylgalactosamine to N-acetylglucosaminolactone or N-acetylgalactosaminolactone in the presence of NAD+ and, at the same time, reduces the NAD+ to NADH.

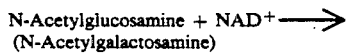
N-Acetylglucosamine + NAD+ ⟶
(N-Acetylgalactosamine)

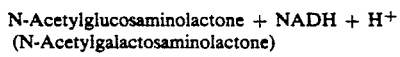
N-Acetylglucosaminolactone + NADH + H+
(N-Acetylgalactosaminolactone)

It exercises no action at all or hardly exercises an action on N,N'-diacetylchitobiose, hexosamine and neutral sugars, except that it exercises only a slight action upon N-acetylmannosamine.

(2) Optimum pH and Stable pH Range

Figure 1:
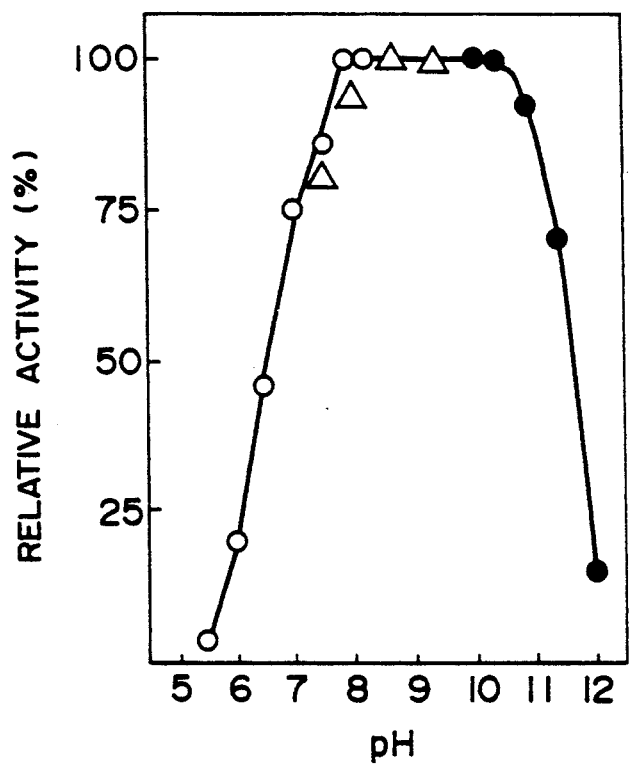
FIG. 1 is graph illustrating the optimum pH of the enzyme of this invention.

FIG. 1 illustrates the results of measurement of enzymatic activity using phosphate buffer, trishydrochloric acid buffer and glycine-sodium hydroxide buffers. As shown in FIG. 1, optimum pH is 8.0–10.5.

Figure 2:
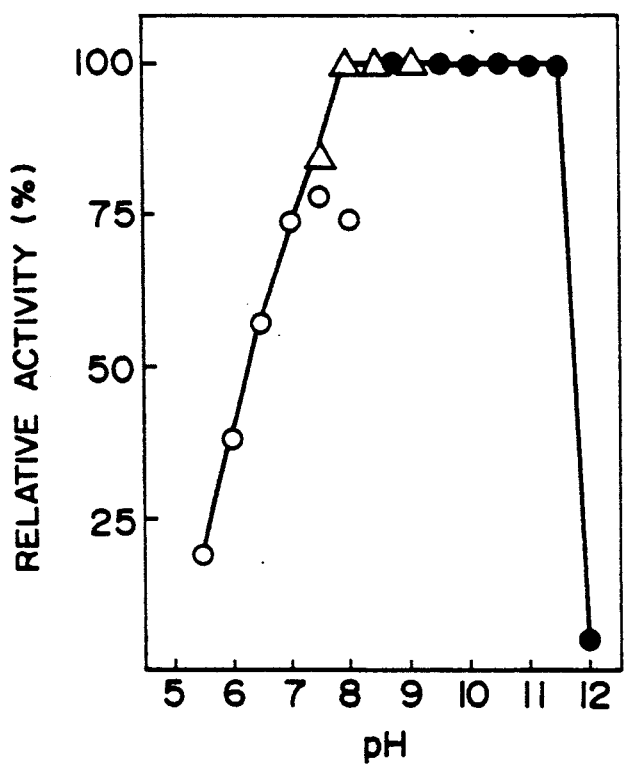
FIG. 2 is a graph illustrating its stable pH.

As shown in FIG. 2, stable pH range is 8.0–11.5.

The buffers used in FIG. 2 were potassium phosphate buffer, tris-hydrochloric acid buffer and glycine-sodium hydroxide buffer.

(3) The Range of Optimum Action Temperature

Figure 3:
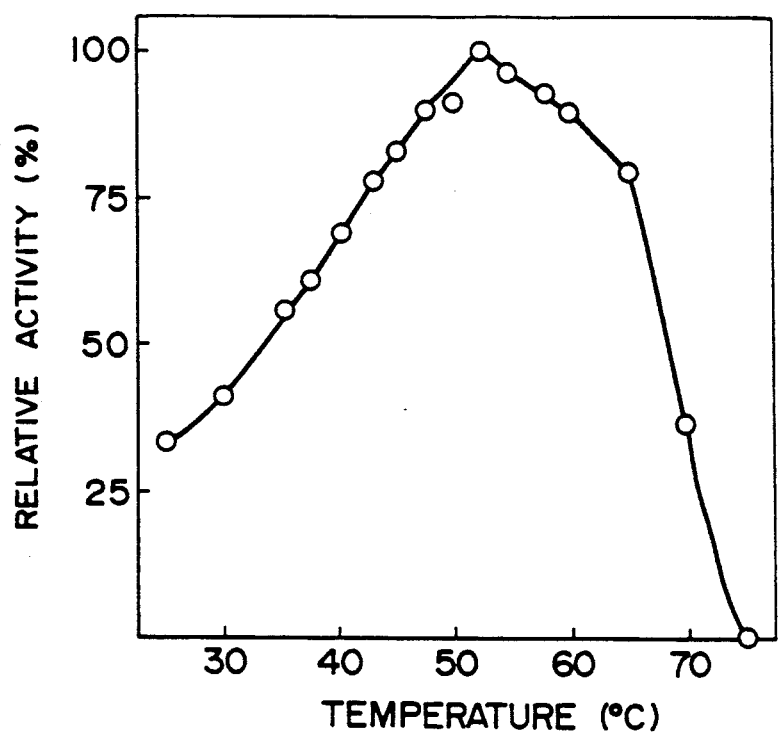
FIG. 3 is a graph illustrating the optimum action temperature range of the enzyme.

As shown in FIG. 3, it is 30° C. to 60° C.

(4) Inactivation Conditions by pH, Temperature, etc.

Figure 4:
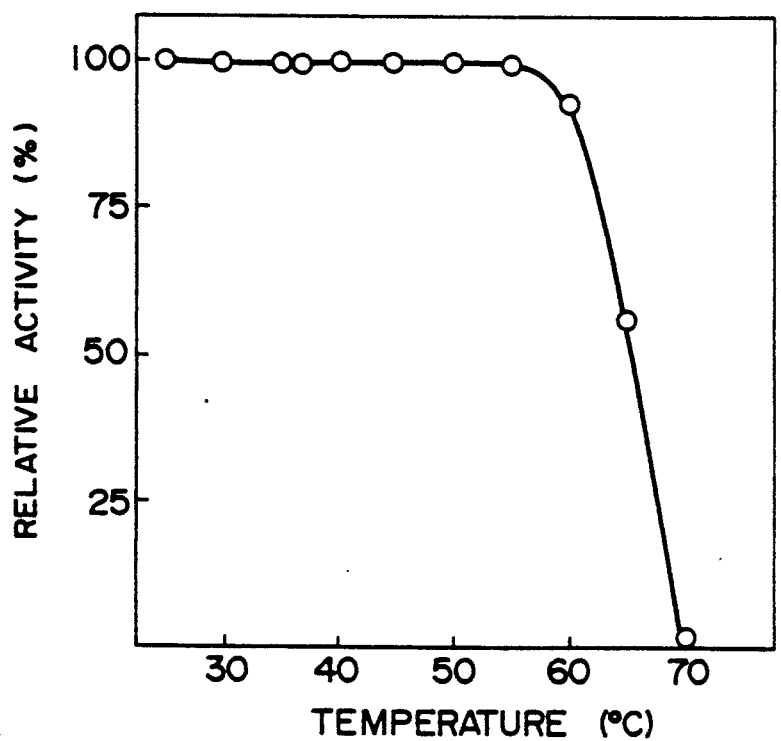
FIG. 4 is a graph illustrating heat stability of the enzyme.

When heated for a period of 10 minutes in 0.1 M glycine-sodium hydroxide buffer (pH 9.5), the enzyme keeps stable up to a temperature of 55° C., while it rapidly loses its activity at 65° C. When heated for a period of 10 minutes at 45° C., it is stable at a pH value of 8.0–11.5, while it is particularly instable at a ph value of 6.0 or below. (FIG. 4)

(5) Influence of Inhibitor and Stabilization

| Inhibitor | Residual activity |
|---|---|
| None | 100% |
| HgCl$_2$ | 35 |
| CdSO$_4$ | 92 |
| ZnSO$_4$ | 95 |
| CaCl$_2$ | 95 |
| CuSO$_4$ | 94 |
| MnSO$_4$ | 96 |
| NaN$_3$ | 89 |
| SDS | 62 |
| KCN | 103 |
| EDTA | 101 |
| PCMB | 97 |
| Iodoacetamide | 104 |
| α, α'-Dipyridyl | 107 |
| o-Phenanthroline | 104 |
| 8-Hydroxyquinoline | 110 |

In the table presented above, enzyme activity was measured in a solution containing 2 mM of metallic ion or inhibitor. There is known no substance particularly contributing to activation and stabilization.

(6) Method of Purification

This enzyme can be isolated and purified according to usual methods. For example, purifying means such as column chromatography using DEAE-cellulose, precipitation using ammonium sulfate, column chromatography using DEAE-Sephadex, gel filtration using Sephadex G-200, etc. are adopted either alone or in appropriate combination.

(7) Molecular Weight

Molecular weight measured by gel filtration using 0.05M tris-hydrochloric acid buffer (containing 0.1M sodium chloride) is about 120,000–130,000.

(8) Polyacrylamide Gel Electrophoresis

Figure 5:
FIG. 5 is a diagram illustrating its electrophoretic band.

As shown in FIG. 5, this substance nearly one band in the chart of usual acrylamide disc electrophoresis using 7.5% polyacrylamide gel. When Bromphenol Blue is used as a standard in 7.5% acrylamide gel, its relative mobility is 0.41.

(9) Isoelectric Point

As measured by polyacrylamide gel isoelectrofocusing, its isoelectric point is 4.7.

(10) Measurement of Activity

To 1.8 ml of 0.1 M glycine-sodium hydroxide buffer (pH 9.5) is added 0.1 ml of 60 mM NDA+ solution. After keeping the mixture at 37° C. for 10 minutes, 10 microliters of enzyme solution is added, and subsequently 0.1 ml of 0.3M N-acetylglucosamine solution is mixed to start the reaction. The reaction mixture is immediately transferred into an absorbance measurement cell (1 cm path) kept at 37° C., and absorbance is measured at intervals of one minute at a wavelength of 340 nm over a period of 5 minutes or, if desired, over a longer period of time. A quantity of enzyme capable of forming one micromole of NADH per one minute is taken as "one unit".

As has been mentioned above, the enzyme of this invention is a novel enzyme of which action and substrate specificity have hitherto been unknown at all.

Next, the process for producing the novel enzyme N-AHDH of this invention will be mentioned. The microorganism used is a strain belonging to Genus Pseudomonas and having an ability to produce N-AHDH. As its concrete example, Pseudomonas sp. No. 53 can be referred to. Varieties and mutant strains of said strain are also usable. Pseudomonas sp. No. 53 is a strain which the present inventors have isolated from soil, and its bacteriological properties are as follows.

(a) Morphology

Microscopic observations (after culture at 30° C. for 18 hours in a glucose-bouillon medium containing 0.4% yeast extract):

(1) Size of cell: Rod having a size of 1.0–1.1 × 1.4–2.6 microns (2) Polymorphism of the cell: The shape of cell ranges from nearly spherical one to relatively long rod. Two-membered chains linked at ends are observable, though longer chain are not observed.

(3) Motility: Quick linear motion (polar flagella).

(4) Spore: Not formed.

(5) Gram-stain: Negative.

(6) Acid-fast: Negative.
(b) State of growth in various media
(1) Bouillon-agar plate culture (3 days at 30° C.): White-brown colored, entire, convex, semi-transparent colonies (1.5 mm in diameter) are formed, without formation of pigment.
(2) Glucose-bouillon-agar plate culture with 0.4% yeast extract (3 days at 30° C.): White-brown colored, entire, convex, semi-transparent colonies (2.1 mm in diameter) are formed.
(3) Glucose-bouillon-agar slant culture with 0.4% yeast extract (24 hours at 30° C.): Good growth, smooth surface, fatty gloss, semi-transparent.
(4) Culture in glucose-bouillon liquid medium with 0.4% yeast extract: In standing culture (2 days at 30° C.), the growth is very bad. A membrane-like substance is slightly formed on the surface, and it precipitates with time. In shaking culture (24 hours at 30° C.), a uniform good growth is observed.
(5) Bouillon-gelatin stab culture (3 days at 24° C.): A slight growth is observed without liquefaction of gelatin.
(6) Lithmus milk (5 days at 30° C.): A slight acid reaction, with a weak coagulation and separation of transparent liquid on the surface.
(c) Physiological properties
(1) Reduction of nitrates: Negative.
(2) Denitrification: Negative.
(3) MR test: Negative.
(4) VP test: Negative.
(5) Formation of indole: Negative.
(6) Formation of hydrogen sulfide: Positive (lead acetate test paper).
(7) Hydrolysis of starch: Negative.
(8) Utilization of citric acid: Negative.
(9) Utilization of inorganic nitrogen source: Negative.
(10) Formation of pigment: Negative.
(11) Urease: Negative.
(12) Oxidase: Positive.
(13) Catalase: Positive.
(14) Growing condition range: 13° C.–36° C. (optimum temperature 29° C.); pH 4.6–8.5 (optimum pH: around neutrality)
(15) Behavior to oxygen: Very aerobic.
(16) O-F test: Oxidative.
(17) Formation of acid and gas from sugar:

|  | Acid formation | Gas formation |
|---|---|---|
| 1. L-Arabinose | + | − |
| 2. D-Xylose | + | − |
| 3. D-Glucose | + | − |
| 4. D-Mannose | + | − |
| 5. D-Fructose | + | − |
| 6. D-Galactose | + | − |
| 7. Maltose | + | − |
| 8. Sucrose | + | − |
| 9. Lactose | + | − |
| 10. Trehalose | + | − |
| 11. D-Sorbitol | − | − |
| 12. D-Mannitol | − | − |
| 13. Inositol | − | − |
| 14. Glycerine | − | − |
| 15. Starch | − | − |

(d) Other properties
(1) No accumulation of poly-β-hydroxybutyric ester.
(2) No formation of fluorescent pigment.
(3) no growth at 40° C.
(4) No utilization of $H_2$ as energy source.
(5) No production of alginine-dihydrolase.

By comparing the above-mentioned taxonamic properties of this novel strain having an N-AHDH-producing ability with the classification mentioned in "Bergey's Manual of Systematic Bacteriology, (1984), Vol. 1", this strain is considered belonging to Genus Pseudomonas. because it is a gram-negative, aerobic, catalase-positive bacillus having polar flagellum and forming no spore. It is considered to be a related species of *Pseudomonas stutzeri*, because it accumulates no poly-β-hydroxybutyrate in cell body, produces no yellow pigment nor fluorescent pigment, utilizes glucose for its growth, and does not grow at 40° C. However, it differs from *Pseudomonas stutzeri* in the points of denitrification, starch degradation and trehalose utilization. Accordingly, it is considered to be a novel strain hitherto unknown.

For the above-mentioned reasons, the inventors named this strain "Pseudomonas sp. No. 53". Pseudomonas sp. No. 53 has been deposited in Fermentation Research Institute, Agency of Industrial Science Technology, Ministry of International Trade & Industry, Japan under the Budapest Treaty as FERM BP-2057.

Next, the culture medium used in this invention may be any of synthetic and natural media, so far as they appropriately contain carbon source, nitrogen source, inorganics and other nutrients. As the carbon source, glucose, galactose, fructose and the like can be used. As the nitrogen source, nitrogen-containing organic substances such as peptone, digested casein, glutamic acid, yeast extract and the like can be used successfully. As the inorganics, salts of sodium, potassium, magnesium, magnanese, calcium, iron and the like can be used.

In this invention, N-AHDH can be obtained in a high yield when a strain having an ability to produce N-AHDH is cultured in a medium containing N-acetylglucosamine or N-acetylgalactosamine. As a preferable example of the culture medium, a medium containing 0.5% of N-acetylglucosamine, 0.5% of yeast extract, 0.3% of peptone, 0.2% of potassium primary phosphate, 0.05% of magnesium sulfate, 0.01% of calcium chloride and 0.01% of ferrous sulfate (pH 7.0) can be referred to. When aeration agitation culture is carried out in said medium at 30° C. for 20 hours, the production titer achieved is 10 to 100 times as high as that achievable by replacing the N-acetylglucosamine with other sugars than N-acetylgalactosamine.

Temperature of the culture is usually in the range of 20° C. to 35° C., and preferably about 30° C. At the start of culture, pH is usually in the range of 6 to 8, and preferably about 7. If shaking culture or submerged agitation culture is carried out under the above-mentioned conditions for 20 to 30 hours, N-AHDH is formed and accumulated in the cultured product.

Since N-AHDH usually exists in bacterial cell, it is preferable to isolate bacterial cell only by centrifugation or filtration. Then, the isolated bacterial cell is broken and solubilized in an appropriate buffer solution to release the enzyme into solution.

In breaking bacterial cell, physical means such as Dynomill, French press, ultrasonic wave and the like, chemical means such as Triton X-100, sodium lauryl sulfate, EDTA and the like, and enzymatic means such as lysozyme and the like may be used either alone or in combination. After breaking the bacterial cell, nucleic acid is removed from the liquid in the usual way and insoluble matter is removed by filtration or centrifugation. Thus, N-AHDH is obtained.

If desired, the N-AHDH may be purified by conventional means for isolation and purification of enzyme, such as (1) column chromatography using DEAE-cellulose column, (2) fractional precipitation using ammonium sulfate, (3) column chromatography using DEAE-Sephadex column, (4) gel filtration using Sephadex, or other methods which may be combined if desired.

Next, the method for the quantitative analysis of N-acetylglucosamine or N-acetylgalactosamine according to this invention and the kit for use in the quantitative analysis may be explained concretely.

The measurement according to this invention is based on the following principle:

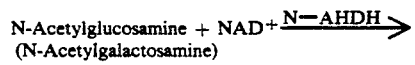
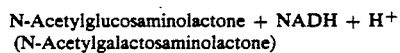

That is, N-acetylglucosamine or N-acetylgalactosamine in sample is reacted with N-AHDH, and the formed NADH is determined according to a known method such as measurement of ultraviolet light adsorbance at 340 nm, etc.

Alternatively, sample is contacted with N-AHDH held on a solid, and the resulting NADH is similarly determined. If desired, an appropriate quantity of inhibitor such as oxamic acid, oxalic acid and the like may be added in order to prevent the influence of the coexisting lactate dehydrogenase (LDH).

As the N-AHDH used in the invention, N-AHDH of any origin may be used. It is preferable to use, however, an N-AHDH obtained by culturing a strain selected from bacteria belonging to Genus Pseudomonas.

As examples of the enzyme-producing bacteria belonging to Genus Pseudomonas. Pseudomonas sp. No. 53 (FERM BP-2057) and the like can be referred to.

In reacting the N-AHDH upon N-acetylglucosamine or N-acetylgalactosamine in sample, the reaction is carried out at a temperature of 60° C. or below at a pH value of 7–11 and preferably at a temperature of 30°–55° C. at a pH value of 8–10.5, usually for a period of about 1–20 minutes. For regulating the pH value, an arbitrarily selected buffer solution which can maintain the above-mentioned pH range and does not disturb the enzyme reaction is used. For example, potasisum phosphate buffer, tris-hydrochloric acid buffer, glycine-sodium hydroxide buffer and the like are preferably used.

The NADH formed by the action of N-AHDH may be determined by any methods. Most usually, however, it is determined by the absorbance measurement at an ultraviolet wavelength of 340 nm. As methods for determining NADH after converting it to a pigment having an absorption in the visible region, a method which comprises reacting it with phenazine methosulfate and nitro blue tetrazolium and measuring the absorbance of the resulting diformazan at 570 nm and a method which comprises reacting it with NADH oxidase [J. Biochem., 98, 1433 (1985)] or phenazine methosulfate or an electron carrier resembling it in action or a metallic ion to form hydrogen peroxide, developing a color from the hydrogen peroxide in the presence of peroxidase and various chromogens and measuring absorbance at the respective optimum wavelengths can be referred to.

When NADH is converted to hydrogen peroxide, it can be detected also by emission spectrometry after treating it with luminol. It is also possible to detect it semi-quantitatively by adding a series of appropriately selected plural redox indicators and electron carrier and observing the color tone of the system. All these methods may be selected and used with reference to their characteristic features.

The kit of this invention for the quantitative analysis of N-acetylglucosamine or N-acetylgalactosamine is constituted of N-AHDH, NAD+, enzymes and reagents for determining resulting NADH and buffering reagents for smoothing progress of their reactions. The reagents and enzymes have a form of liquid composition, solid composition or freeze-dried composition, and they are dissolved and mixed into a buffer solution just before use to make a reagent for measurement, in accordance with need.

In practising the measurement, the kit is directly reacted upon a sample containing N-acetylglucosamine or N-acetylgalactosamine to form NADH. Then, NADH in the reaction mixture is measured either directly or after adding a NADH-determining reagent. The measurement may be carried out either by one reagent system or by two reagent system or by multi-reagent system.

According to this invention, N-acetylglucosamine or N-acetylgalactosamine can be quantitatively analyzed in a high accuracy by the use of a novel N-AHDH and, on its basis, activity of $\beta$-N-acetylglucosaminidase, etc., can be measured. Thus, structure of complex sugars can be analyzed and pathois of renal disorder can be diagnozed, effectively. Accordingly, this invention is very worthwhile for specialists in the art.

Next, this invention will be illustrated by way of the following examples.

EXAMPLE 1

Pseudomonas sp. No. 53 (FERM BP-2057) was inoculated into a 150 ml Erlenmeyer flask oontaining 20 ml of a seed medium (pH 7.2) containing 0.5% of N-acetylglucosamine, 0.5% of yeast extract, 0.3% of peptone, 0.2% of potassium dihydrogen phosphate, 0.05% of magnesium sulfate, 0.01% of calcium chloride and 0.01% of ferrous sulfate. After a shaking culture at 30° C. for 24 hours, the mixture was planted into a jar fermenter (manufactured by Iwashiya Seibutsukagaku K.K.) containing 2 liters of the same medium as above, and subjected to an aeration (2 liters/minute) agitation (500 r.p.m.) culture at 30° C. for 18 hours. The N-AHDH thus produced was accumulated in the bacterial cell.

EXAMPLE 2

Five liters of 0.02M tris-hydrochloric acid buffer (pH 8.0) (hereinafter it is referred to as "standard buffer") was added to 0.96 kg of alive bacterial cells obtained in the same manner as in Example 1. Then, Triton X-100 and EDTA were added so that their concentrations came to 0.5% and 10 mM, respectively. By stirring the mixture overnight at a low temperature (5° C.), a uniform suspension was obtained. Then, it was broken at 3,000 r.p.m. by means of Dynomill (manufactured by Willey A. Beckohen Co., Switzerland). By centrifuging it at 8,000 r.p.m. for 20 minutes, 5.1 liters of a supernatant was obtained.

Then, 3.5 kg of wet DEAE-cellulose was added thereto and pH of the mixture was adjusted to 8.0, after which it was stirred for 30 minutes to have the enzyme adsorbed onto the DEAE-cellulose. The DEAE-cellulose was collected by filtration by means of Buchner funnel and washed with 10 liters of standard buffer, after which it was washed with 7 liters of standard buffer containing 0.3 M of sodium chloride and the washing was taken out as an intended fraction. This fraction was concentrated to a volume of 1.4 liters by means of Hollow Fiber Ultrafilter (manufactured by Asahi Kasei Kogyo K.K.). Then 112 g of powdery ammonium sulfate was dissolved into the concentrate and thoroughly stirred.

After allowing the mixture to stand for 2 hours, it was centrifuged at 9,000 r.p.m. for 20 minutes to obtain 1.4 liters of supernatant. Then, an additional 364 g of ammonium sulfate was added and completely dissolved thereinto, and the resulting solution was allowed to stand overnight at a low temperature.

The resulting precipitate was collected by centrifuging the mixture at 12,000 r.p.m. for 20 minutes, and it was dissolved into 1.4 liters of standard buffer containing 4% ammonium sulfate. Then, it was passed through a column (9 cm in diameter, 40 cm in height) of Phenyl-Sepharose CL-4B (manufactured by Pharmacia, Sweden) previously equilibrated with a standard buffer containing 6% ammonium sulfate to have the enzyme adsorbed on the column, and then it was eluted with 20 liters of standard buffer simultaneously having a concentration gradient of 0 to 30% with regard to ethylene glycol and an inverse concentration gradient of 4 to 0% with regard to ammonium sulfate.

The active fractions were collected, united, and concentrated to 0.5 liter by means of ultrafiltration, after which the enzyme solution was subjected to a filtration dialysis against 3 liters of standard buffer containing 0.1 M sodium chloride. The dialyzed solution was passed through a column (9 cm in diameter, 30 cm in height) of DEAE-Sephadex A-50 previously equilibrated with standard buffer containing 0.1 M sodium chloride to have the enzyme adsorbed on the column, and it was eluted with 20 liters of standard buffer having a sodium chloride concentration gradient of 0.1 M to 0.3 M.

The active fraction was concentrated to 50 ml by ultrafiltration, and its 5 ml portion was subjected to a preparative electrophoresis, using an apparatus manufactured by Fuji Riken K.K., to separate and recover protein by polyacrylamide disc electrophoresis.

The polyacrylamide gel used in this operation was a 7.5% gel. The current was 10 mA, and the buffer used for recovery was 0.012 M tris-0.1 M glycine buffer (pH 8.3).

The active fraction thus recovered was concentrated by ultrafiltration, and additionally concentrated to 1 ml by means of collodion bag concentrating apparatus. The concentrate was subjected to gel filtration by the use of a column (2.5 cm in diameter, 95 cm in height) of Sephadex G-200 containing 0.1 M sodium chloride.

All the crude enzyme solutions were purified by similar treatment. The active fractions were collected and concentrated to obtain 1,980 units of a purified enzyme. As shown in FIG. 5, it was an enzyme sample showing nearly one band in polyacrylamide gel disc electrophoresis.

EXAMPLE 3

Concentration of N-acetylglucosamine in solution was determined by the following method by the use of the following reagents.

| | |
|---|---|
| 0.1M Potassium phosphate buffer (pH 7.4) | 1.7 ml |
| NAD+ (60 mM) | 0.1 ml |
| N-AHDH (250 units/ml) | 0.1 ml |
| Sample solution | 0.1 ml |

2. Method of Quantitative Analysis

Figure 6:
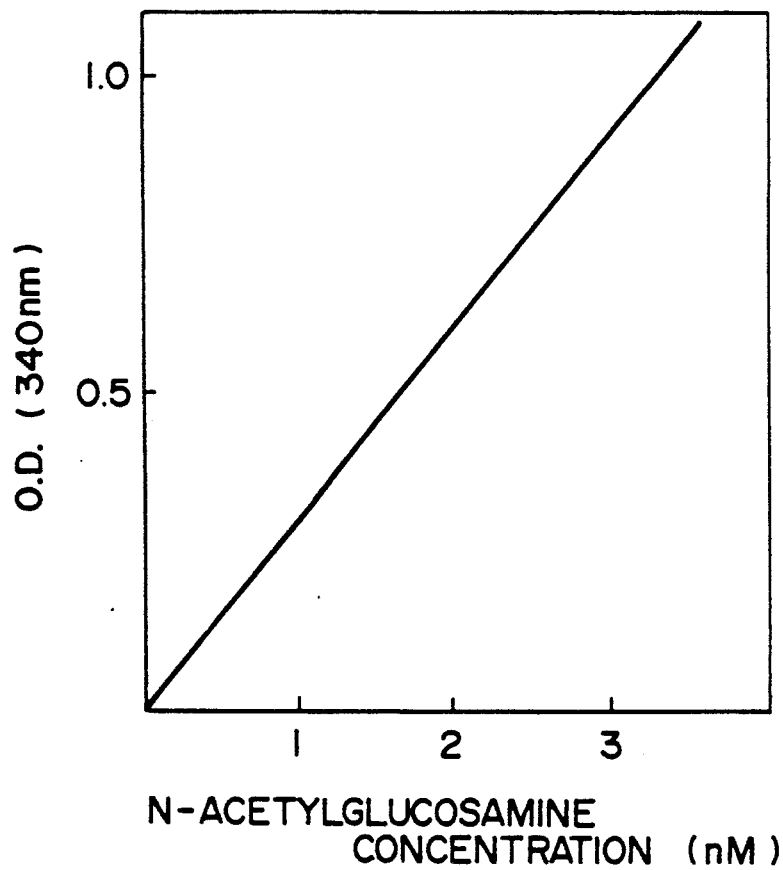
FIG. 6 is calibration curve in Example 3; provided that the buffer solutions used in FIG. 1 and FIG. 2 are potassium phosphate buffer (o—o), tris hydrochloric acid buffer ($\Delta$—$\Delta$) and glycine-sodium hydroxide buffer ( — ).

Predetermined quantities of the reagents were taken into a test tube and reacted at 37° C. for 10 minutes, after which absorbance was measured at 340 nm. Net absorbance of sample solution was calculated by deducting, from it, absorbance in a run using the same quantity of water in place of sample solution. On the other hand, a calibration curve was prepared by treating N-acetylglucosamine solutions of known concentrations in the same manner as above. By referring to the calibration curve, concentration of N-acetylglucosamine in sample solution was determined. FIG. 6 illustrates the calibration curve.

EXAMPLE 4

Concentration of N-acetylgalactosamine in solution was determined by the following method by the use of the following reagents.

| | |
|---|---|
| 0.1M Potassium phosphate buffer (pH 8.0) (containing 0.3% of Triton X-100) | 115 microliters |
| Phenazine Methosulfate (1 mg/ml) | 5 microliters |
| Nitro Blue Tetrazolium (10 mg/ml) | 5 microliters |
| NAD+ (60 mM) | 10 microliters |
| N-AHDH (155 units/ml) | 15 microliters |
| Sample solution | 50 microliters |

2. Method of Quantitative Analysis

Predetermined quantities of reagents were taken into a test tube and reacted at 37° C. for 15 minutes. Then, 2.0 ml of 0.3 N hydrochloric acid was added and thoroughly stirred. Absorbance of the resulting color was measured at 570 nm. In parallel with it, the same quantity as above of water, in place of sample solution, was similarly treated and its absorbance was taken as blank. By deducting the blank from the above-mentioned absorbance of sample solution, net absorbance of sample solution was calculated. On the other hand, a calibration curve was prepared by similarly treating N-acetylgalactosamine solutions of known concentrations. By referring to the calibration curve, concentration of N-acetylgalactosamine in sample solution was determined.

EXAMPLE 5

Activity of β-N-acetylglucosaminidase extracted from the bovine kidney was determined by the following method by using the following reagents.

1. Reagents

| | |
|---|---|
| A. 0.1M Sodium citrate buffer (pH 4.4) | 0.3 ml |
| N,N'-Diacetylchitobiose (50 mM) | 0.1 ml |

-continued

|   | Sample solution | 0.1 ml |
|---|---|---|
| B. | 0.2M Glycine-sodium hydroxide buffer (pH 10.0) | 1.3 ml |
|   | NAD⁺ (60 mM) | 0.1 ml |
|   | N-AHDH (250 units/ml) | 0.1 ml |

2. Method of Quantitative Analysis

Predetermined quantities of the reagents A were taken into a test tube and reacted at 37° C. for 15 minutes. Then, predetermined quantities of reagents B were mixed together, and the resulting mixture was added to the test tube and again reacted at 37° C. for 10 minutes. Absorbance was measured at 340 nm, from which absorbance of a run using water in place of sample solution was deducted to give net absorbance of sample solution. Enzyme activity of sample solution was calculated from the following equation:

$$\frac{O.D.}{3.11} \times \frac{1}{15} \times \frac{1}{2} \times 10 = \frac{O.D.}{9.33} \text{ (Units/ml)}$$

We claim:

1. Purified N-acetylhexaosamine-dehydrogenase which takes off hydrogen from N-acetylglucosamine or N-acetylgalactosamine to convert them to N-acetylglucosaminolactone or N-acetylgalactosaminolactone, respectively, and at the same time reduce co-enzyme NAD⁺ to NADH, of which optimum pH is 8.0 to 10.5, and of which stable pH is 8.0 to 11.0.

2. A method for the quantitative analysis of N-acetylglucosamine or N-acetylgalactosamine which comprises reacting the N-acetylhexosamine-dehydrogenase of claim 1 upon a sample containing N-acetylglucosamine or N-acetylgalactosamine and measuring the quantity of the resulting NADH.

3. A kit for use in the quantitative analysis of N-acetylglucosamine or N-acetylgalactosamine which comprises the N-acetylhexosamine-dehydrogenase of claim 1, NAD⁺ and a buffer solution.

4. A process for producing N-acetyl hexosamine dehydrogenase which comprises culturing a strain Pseudomonas sp. No. 53 (FERM BP-2057) having an ability to produce N-acetylhexosamine-dehydrogenase in a culture medium and collecting N-acetylhexosamine dehydrogenase from the cultured product.

5. The purified N-acetylhexaosamine-dehydrogenase of claim 1 having a molecular weight of about 120,000 to 130,000 as measured by gel filtration method.

* * * * *